United States Patent [19]

Pearson et al.

[11] Patent Number: 4,821,564

[45] Date of Patent: Apr. 18, 1989

[54] METHOD AND SYSTEM FOR DETERMINING FLUID PRESSURES IN WELLBORES AND TUBULAR CONDUITS

[75] Inventors: C. M. Pearson; Fevzi Zeren; Ahmed S. Abou-Sayed, all of Plano, Tex.

[73] Assignee: Atlantic Richfield Company, Los Angeles, Calif.

[21] Appl. No.: 113,782

[22] Filed: Oct. 26, 1987

Related U.S. Application Data

[62] Division of Ser. No. 829,381, Feb. 13, 1986, Pat. No. 4,726,219.

[51] Int. Cl.$^4$ .......................................... E21B 47/00
[52] U.S. Cl. ......................................... 73/155; 73/55
[58] Field of Search ............... 73/155, 55, 53, 198; 166/308

[56] References Cited

U.S. PATENT DOCUMENTS

| | | | |
|---|---|---|---|
| 1,863,090 | 6/1932 | Albersherm et al. | 73/55 |
| 3,468,158 | 9/1969 | Chien | 73/55 |
| 3,548,638 | 12/1970 | Uchida et al. | 73/55 |
| 3,839,914 | 10/1974 | Modisette et al. | 73/438 |
| 3,926,050 | 12/1975 | Turner et al. | 73/861.04 |
| 3,952,577 | 4/1976 | Hayes et al. | 73/55 |
| 4,641,535 | 2/1987 | Malguarnera | 73/861.52 X |

FOREIGN PATENT DOCUMENTS 2728670  1/1979  Fed. Rep. of Germany .......... 73/55

OTHER PUBLICATIONS

Scheve et al., "A Simplified Continuous Viscometer for Non-Newtonian Fluids", Industrial and Eng. Chem., Fundamentals, vol. 13, No. 2, pp. 150–154, May 1974.

Primary Examiner—Eugene R. LaRoche
Assistant Examiner—Seung Ham
Attorney, Agent, or Firm—Michael E. Martin

[57] ABSTRACT

Friction pressure losses are obtained for non-Newtonian or generalized Newtonian fluids being pumped through conduits at high flow rates, such as in hydraulic fracturing of subterranean formations, by measuring friction pressure losses in a pipe viscometer under laminar flow conditions. The pipe viscometer includes a pump which supplies fluid to a continuous loop having three pipe sections of different diameter for measuring pressure drop at different flow velocities. Sets of data points of generalized shear stress and shear rate are measured for determining the consistency index (K") and the Power Law or flow behavior index (n'). The generalized Reynolds number of the fluid being pumped is determined using the values of consistency index and flow behavior index and this Reynolds number is maintained in a second pipe viscometer section arranged in parallel with the laminar flow loop by pumping the same fluid wherein the second pipe viscometer section has the same roughness as the conduit through which friction pressure loss is to be determined. The Fanning friction factor (f) is determined for the pipe viscometer section from known values of friction pressure drop over a predetermined length of the pipe viscometer section at a known flow velocity, known fluid density and known hydraulic radius of the pipe viscometer section. The actual pressure drop over a predetermined length of conduit is determined using the calculated value of friction factor (f) and measured values of fluid density, flow velocity and conduit dimensions.

13 Claims, 2 Drawing Sheets

METHOD AND SYSTEM FOR DETERMINING FLUID PRESSURES IN WELLBORES AND TUBULAR CONDUITS

This is a division of application Ser. No. 829,381, filed Feb. 13, 1986, now U.S. Pat. No. 4,726,219.

BACKGROUND OF THE INVENTION

1. Field of the Invention

The present invention pertains to a method and system for determining the friction pressure losses in fluids being pumped through generally tubular conduits, including non-Newtonian drilling and fracturing fluids used in the production of subterranean hydrocarbon deposit.

2. Background

In the production of oil and gas from subterranean deposits it is important to be able to determine the actual fluid pressure at a particular point in the wellbore which may be several thousand feet below the surface. In particular, it is important to know the so-called bottom hole pressure in an injection well or during fracturing of a formation with pumped fluids. There are also other operations where direct measurement of fluid pressure loss in a conduit is not easily obtainable at the desired point in the conduit.

In oil and gas well stimulation operations involving formation fracturing, large quantities of non-Newtonian fluids or generalized Newtonian fluids are pumped down the wellbore at relatively high velocities. The actual pressure of the fluid at the point of injection is the measured pressure at the wellhead plus the hydrostatic pressure of the fluid column minus the friction pressure loss between the point of measurement and the point of injection deep in the wellbore. So-called bottom hole pressure is important to determine in regard to determining the response of a formation to the treatment process and for purposes of conducting an analysis of the geometry of the fracture propagation.

Conventional techniques for determining fluid friction pressure losses in a wellbore include determining readily obtainable parameters such as the flow velocity and the geometry of the conduit through which the fluid is being pumped. These factors, together with laboratory measurement of flow indices for predetermined types of fluids, have been used to calculate predicted friction pressure losses in the wellbore before fracturing type stimulation techniques as well as other fluid pumping operations which require relatively accurate determination of pressure at a particular point in a conduit.

Although flow indices such as the consistency index (K') and the so-called Power Law index or flow behavior index (n') may be obtainable for a particular fluid composition from laboratory measurements, the characteristics of fluids actually used in an operation may vary substantially thereby resulting in relatively serious errors in friction pressure loss calculations. Recent developments in the provision of inline pipe viscometers have been of some assistance in determining friction pressure losses.

In oil and gas well hydraulic formation fracturing operations, in particular, and certain other operations involving the use of fluids which behave generally according to the so called Power Law or Ostwald-de Waele model, the fluid characteristics typically change on site during the operation. Accordingly, the use of predetermined consistency and flow behavior indices not only introduce serious pressure calculation errors, but the use of various measuring devices which are disposed directly in the flow line such as inline pipe viscometers is precluded by the presence of abrasives in the fluid such as sand proppants and the like which damage or destroy the measuring devices after only brief periods of use.

Accordingly, there has been an acute need to develop improved methods of determining fluid friction pressure losses which occur in subterranean formation fracturing operations and similar operations wherein direct pressure measurements at the desired points to be considered are not readily obtainable. It is to this end that the present invention has been developed which provides an improved process and system to provide for determining pressure losses in a flowing fluid stream due to pipe friction and other energy losses due to fluid flow through tubular conduits and the like, including subterranean wellbores.

SUMMARY OF THE INVENTION

The present invention provides an improved method for determining fluid pressure losses in conduits such as subterranean wellbores by determining the rheological properties including the flow behavior index and the consistency index, using these indices to determine the Reynolds number of the fluid being pumped through the conduit, conducting flow at the same Reynolds number through a pipe viscometer having the same roughness characteristics as that of the conduit or wellbore and measuring the friction pressure loss and the viscosity to determine the Fanning friction factor for laminar and turbulent flow in the pipe viscometer. The friction factor and parameters such as effective pipe diameter, pipe length, fluid density and velocity in the conduit where pressure loss is to be determined are then used to determine the actual pressure at the desired point in said conduit.

In accordance with one aspect of the present invention, non-Newtonian and generalized Newtonian fluids such as oil and gas well fracturing fluids are sampled from a flow line leading to the fluid injection well, and the fluid samples are pumped through a pressure loss measuring system wherein, under laminar flow conditions, pressure losses and fluid velocities over a predetermined length of one or more conduits are determined and used to calculate the fluid shear stress and shear rate. The values of shear stress and shear rate are used to determine the consistency index (K') and the flow behavior or Power Law index (n'). These indices are then used in calculating a matching parameter, such as the generalized Reynolds number for the fluid in the conduit for which the pressure loss is to be measured.

The velocity or flow rate required in a pipe viscometer is then determined to provide the same scaling or matching parameter of the flow in the conduit for which losses are to be determined. In this way, pressure losses in the pipe viscometer can be used to determine the Fanning friction factor which can then be used to calculate the actual friction pressure loss in the length of conduit which is to be measured for determination of the actual pressure at the predetermined point in the conduit system.

In accordance with still a further aspect of the present invention, there is provided a system for measuring the flow behavior indices for a non-Newtonian, generalized Newtonian or Power Law fluid by measuring pressure loss over a prescribed length of conduit in one or more sections of conduit at different velocities in laminar flow whereby shear stress and shear rate can be calculated and plotted as a means of determining the values of the flow indices themselves. These flow indices are then used to calculate the generalized Reynolds number for the fluid being conducted through the conduit in question, the dimensions of the conduit, the fluid density, and the fluid velocity in the conduit all being directly measurable. Using the same equation as required to determine the generalized Reynolds number, the velocity required to obtain the same Reynolds number in a pipe viscometer may then be calculated and flow through the pipe viscometer is adjusted to attain the velocity required for the same Reynolds number in the pipe viscometer as is present in the conduit system for which pressure loss is to be determined. Actual pressure drop over a predetermined length of the pipe viscometer may be obtained to calculate the Fanning friction factor since the other factors such as pipe dimensions, fluid density and velocities are known. Pressure drop due to friction over a predetermined length of conduit such as a wellbore is then determined based on the known friction factor, known fluid density, velocity measured at the wellbore entrance and the conduit dimensions such as diameter and length.

The present invention thus provides an improved method for measuring pressure losses involving non-Newtonian or generalized Newtonian fluids pumped through elongated tubular conduits and similar flow path, which method is particularly adapted and useful in determining friction pressure losses in wellbores during the pummping of fracturing fluids and other fluids having flow characteristics which are subject to frequent and rapid changes. Those skilled in the art will recognize the abovementioned features and advantages of the present invention as well as additional superior aspects thereof upon reading the detailed description which follows in conjunction with the drawing.

DETAILED DESCRIPTION OF PREFERRED EMBODIMENTS

Figure 1:
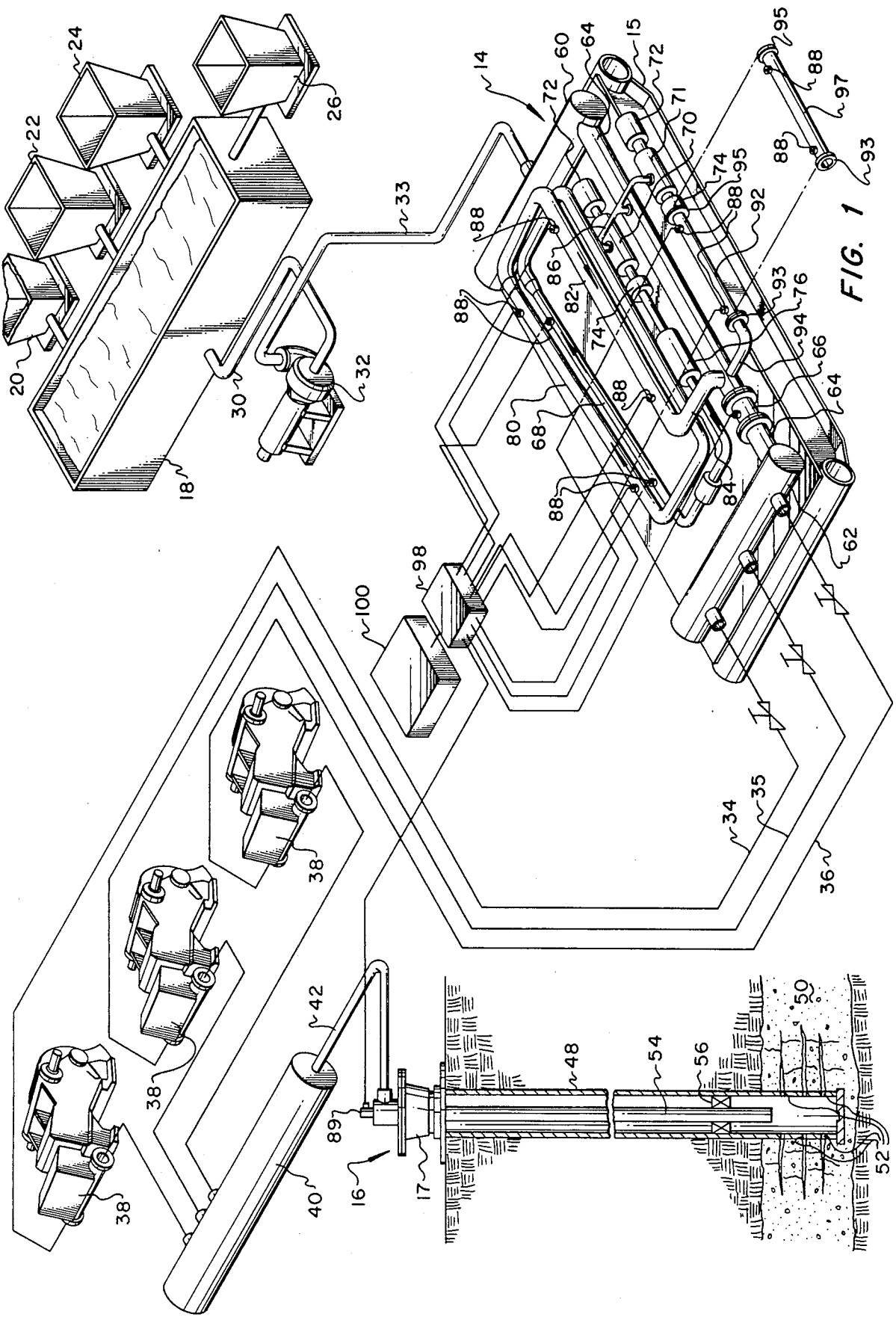
FIG. 1 is a somewhat schematic diagram of a system for determining certain flow behavior indices and friction pressure losses in a wellbore for fluids being pumped down a wellbore in a formation fracturing operation, for example.

Subterranean formations bearing oil, gas and other mineral deposits are often stimulated to enhance the recovery of these substances by hydraulic fracturing of the formation itself. The various types of fluids used in fracturing operations are made up of several constituents including water, gels, corrosion inhibitors, and fracture proppants, which, when mixed or blended together, provide a fluid having unique rheological characteristics. In actual practice in carrying out hydraulic well fracturing operations, the exact composition of the fluid is subject to change through purposeful control or sometimes inadvertant changes in the mix of the fluid constituents. Accordingly, laboratory determined rheological constants are often erroneous and lead to substantial errors in flow calculations such as the calculation of fluid friction pressure losses.

The actual pressure at the point of injection of a fracturing fluid into a subterranean formation is of interest in regard to determining the expected response of the formation to the treatment process and to analyze the geometry of the fracture. Since these fluids are pumped at relatively high and turbulent flow velocities, substantial friction pressure losses may occur in the wellbore, particularly considering that the point of injection in the wellbore with respect to the point of actual convenient measurement of the fluid may cover a distance of several thousand feet. Although total pressure at the surface or at the wellhead can be measured according to conventional techniques and the hydrostatic pressure head can be determined based on knowledge of the point of injection, the actual pressure at the point of injection into the formation has not been easily obtainable and measurement errors on the order of several hundred pounds per square inch, for example, have been experienced in connection with hydraulic fracturing operations. Although the present invention is directed to overcoming problems associated with hydraulic earth formation fracturing using non-Newtonian or generalized Newtonian fluid, the process and apparatus may be utilized in connection with other friction pressure loss measurements in conduits.

The present invention contemplates the determination of the power law constants comprising the consistency index ($K'$) and the Power Law or flow behavior index ($n'$) by plotting values of shear stress versus shear rate for the fluid in question on a logarithmic scale wherein, by definition, the consistency index ($K'$) comprises the intercept of the curve comprising the function of the shear rate versus shear stress with the ordinate. The slope of the curve also defines the Power Law or flow behavior index ($n'$). The shear stress and shear rate may be determined in accordance with the present invention by the provision of a pipe viscometer characterized by three predetermined lengths of pipe, each having a different diameter, whereby over the same given lengths of pipe and the same flow rate, different values of pressure drop and velocity may be determined. Accordingly, wall shear stress may be calculated using the equation:

$$\tau = D\, \Delta P / 4L \quad (1)$$

which is the generalized pipe flow equation for shear stress. Since the diameter of the viscometer pipe and the length of the viscometer pipe over which the pressure drop measurements are made are known quantities, various values of shear stress can be calculated for the respective pressure drop measurements. These values of shear stress at given flow conditions can be plotted against values of shear rate determined from the following equation:

$$\gamma = 8\, V/D \quad (2)$$

which is the shear rate equation for laminar flow in a pipe.

In the equation for shear stress, $D$ = pipe diameter, in.; $\Delta P$ = differential pressure, lbs./in.$^2$; and $L$ = pipe length, in. For the shear rate equation $V$ = velocity, in./sec.; and $D$ = pipe diameter, in.

Figure 2:
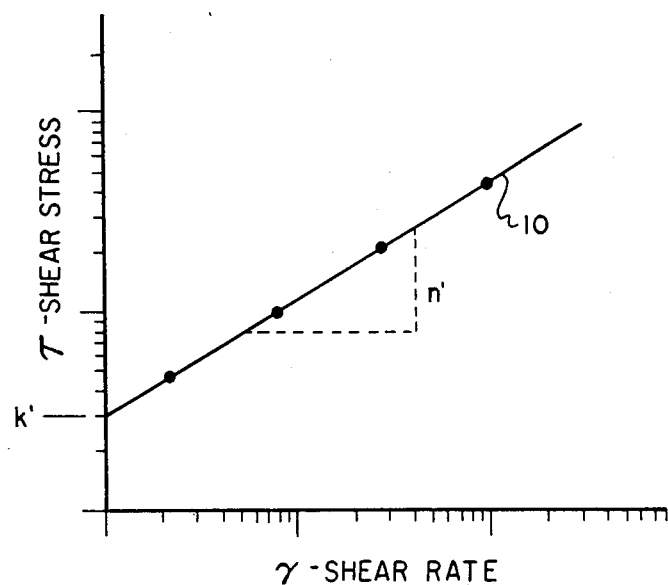
FIG. 2 is an exemplary graphical plot of fluid shear rate versus shear stress on a log-log scale.

FIG. 2 illustrates a typical plot of shear stress as the ordinate and shear rate as the abscissa on a logarithmic versus logarithmic scale wherein the line 10 indicates the shear rate as a function of shear stress and the intercept of the line 10 with the ordinate gives a value of the consistency index (K') and the slope of the line 10 provides the value of the Power Law Index (n'). The provision of at least three separate measurements enables the determination of a suitable fit of the line 10 to obtain accurate values of the respective indices.

The provision of laminar flow in the viscometer pipes used to determine values of shear rate and shear stress may be based on selecting a flow rate which will provide a Reynolds number ($N'_{Re}$) which may be selected to be a value suitably below 2000 by assuming values of the consistency index (K') and the flow behavior index (n') for the fluid being tested. In this regard, known values of these indices for similar fracturing fluids may be utilized and a Reynolds number selected which is well within any normally possible margin of error of the values of the respective indices. Of course, instantaneous values of the consistency index and the flow behavior index may be computed utilizing a digital computer on the basis of measuring flow rate in the laminar flow pipe viscometer to determine velocity and by continuously measuring the pressure drops across the respective pipe lengths to provide the points which define the line 10 in FIG. 2.

With measured values of the consistency index and the flow behavior index available, pressure losses in a length of conduit such as an elongated wellbore may be obtained by calculating the Reynolds number of the fluid being pumped through said conduit, such as a wellbore, using the equation:

$$N'_{Re} = D^{n'} V^{2-n'} \rho / g_c K'(8)^{n'-1} \quad (3)$$

wherein the units of the parameters are as follows: D=in., V=in./sec., $\rho$=fluid density in lbm./in$^3$, and $g_c$=the gravity constant in in./sec./sec.

In accordance with the present invention, it is considered that the matching parameter comprising the generalized Reynolds number ($N'_{Re}$) may be used to determine the velocity in a turbulent flow pipe viscometer having approximately the same ration of hydraulic radius to surface roughness as the conduit in which pressure losses are to be determined. Assuming a Reynolds number ($N'_{Re}$) for the flow in the pipe viscometer to be the same as is encountered in the wellbore, then a pressure drop over a predetermined length of pipe in the pipe viscometer may be measured and the Fanning friction factor (f) calculated using the equation:

$$f = D \Delta P g_c / 2 L \rho V^2 \quad (4)$$

wherein the Fanning friction factor (f) is determined from the measured pressure drop in the pipe viscometer and the parameters of pipe diameter (D), the pipe length (L), over which the pressure drop is measured, the fluid density $\rho$, and the fluid velocity in the pipe viscometer are known quantities. After determining the Fanning friction factor, the same equation may be used to solve for the expected pressure drop in a conduit such as a wellbore wherein the effective wellbore diameter (D), the length of the wellbore (L), fluid density $\rho$, which is the same as the density of the fluid tested in the pipe viscometer, and the fluid velocity (V) all are known or can be readily measured. Accordingly, the equation given above solved in terms of the Fanning friction factor may also be expressed as follows:

$$\Delta P = (f) 2 L \rho V^2 / D g_c \quad (5)$$

wherein $\Delta P$ is the friction pressure drop over the length (L) of conduit or wellbore in question.

Accordingly, by matching the flow regime of the fluid flowing through a conduit such as a wellbore through which the frictional pressure drop is to be measured with the flow regime of a pipe viscometer having the same surface roughness as the wellbore pipe or other conduit, frictional pressure losses for fluids having rheological properties other than known types of fluid may be readily determined.

Referring to drawing FIG. 1, there is illustrated in somewhat schematic form one embodiment of a unique apparatus which may be used in conjunction with the improved method of the present invention. The apparatus is shown in an application for determining the friction pressure loss encountered in pumping formation fracturing fluids into a subterranean hydrocarbon-containing formation. The apparatus for measuring the rheological parameters (K') and (n') is generally designated by the numeral 14 and is shown installed in a system for supplying a fracturing fluid to a well 16. The system typically also includes a fluid blending tank 18 which is supplied with various fluid constituents such as gels, corrosion inhibitors, acids and the like, from supply tanks 20, 22 and 24. Other fluid additives such as proppant materials are typically also supplied from a tank 26. The constituents of the fracturing fluid are blended in tank 18 and are discharged from the blending tank through a conduit 30 to a charging pump 32. The charging pump 32 supplies fluid to the apparatus 14 through a conduit 33 and fluid is discharged from the apparatus 14 through respective conduits 34, 35 and 36 to respective high pressure positive displacement pumps 38. The pumps 38 are preferably adapted to discharge fluid into a manifold 40 at pressures ranging from 5,000 to 10,000 psig, which fluid is supplied through a conduit 42 to the well 16.

The exemplary well 16, shown in somewhat schematic form in FIG. 1, includes a casing 48 extending from a wellhead 17 to a subterranean formation 50. The casing 48 is perforated at a plurality of openings 52 whereby the aforementioned fracturing fluid may be injected into the formation to create generally vertically extending hydraulically formed cracks or crevices which are propped open by the deposition of the proppant included in the fracturing fluid. In the exemplary well 16, the fracturing fluid is supplied through a conduit 54 to a point just above the casing perforations 52. The casing 48 is typically packed off by a suitable seal or packer 56. Those skilled in the art will recognize that the method and system of the present invention may be used in conjunction with various types of conduits wherein fluid is being pumped through an annular flow path as well as through a cylindrical pipe, wherein, in the former case, the equivalent hydraulic radius of a cylindrical pipe is used in specifying the parameter (D) for equivalent conduit diameter.

The viscometer apparatus 14 comprises a conduit system mounted on a suitable frame or skid 15 and preferably includes a fluid inlet manifold 60 connected to the conduit 33. The manifold 60 may also be adapted to be connected to other fluid supply conduits if the apparatus 14 is to be used to measure the indices and the friction factor for different fluids from respective sources at one particular work site. The manifold 60 is connected to a fluid discharge manifold 62 by a main connecting conduit 64 which may have interposed therein an in-line type flow meter 66 of a type commercially available such as a Model 1001465 magnetic flowmeter manufactured by Fischer and Porter Company of Warminster, Pa. The discharge manifold 62 is suitably connected to the pump supply conduits 34, 35 and 36, as illustrated. A laminar flow viscometer arrangement for the apparatus 14 preferably takes the form of a continuous loop including at least three straight conduit sections having different flow passage diameters and which may be constructed of conventional fluid piping used in oilfield and other fluid handling applications. The laminar flow viscometer includes a first conduit section 68 which is adapted to receive fluid from the conduit 64 by way of a pump 70 driven by motor means 72. The pump 70 is preferably of a variable displacement type such as a type made under the trademark Moyno. Conduit 68 is connected to the pump 70 by way of a suitable in-line flow meter 74 similar to the flow meter 66 and a fluid density meter 76 of a type commercially available such as a Model SGO gamma densiometer manufactured by Texas Nuclear Company of Austin, Tex.

The conduit section 68 is connected to a second conduit section of larger diameter and generally designated by the by the numeral 80 which, in turn, is connected to a third conduit section of still larger diameter and designated by the numeral 82. The conduit sections 68, 80 and 82 are connected by suitable conduit reducer or expander sections to form a continuous loop from the pump 70 to a connecting conduit 84 wherein the conduit 82 returns fluid flow to the conduit 64. Fluid is supplied to the pump 70 by way of a suction conduit 86 in communication with the conduit 64 upstream of the fluid return conduit section 84. The conduit sections 68, 80 and 82 are each provided with spaced apart differential pressure measuring transducers 88, which may be of a type commercially available, such as a Model P532 manufactured by Validyne Engineering Corporation of Northridge, Calif. The transducers 88 are located along each of straight runs of the conduit sections 68, 80, and 82 at predetermined points with respect to any bends or elbows in the laminar flow loop to eliminate any flow disturbance effects. The spacing between transducers 88 which are located on the respective conduit sections 68, 80 and 82 are known and are used in conjunction with the equations referenced hereinabove for determining generalized shear stress and shear rate values for determination of the consistency index (K') and the flow behavior index (n'). Those skilled in the art will recognize that other types of pressure differential measuring devices may be used to measure the friction pressure differentials along the aforementioned conduit sections.

The apparatus 14 further includes a turbulent flow pipe viscometer comprising a section of pipe 92 which is interposed in a second pressure differential measuring flow loop between a second axial flow positive displacement pump 71 and a return conduit 94. The second pump 71 is similar to the pump 70 and is also in communication with the suction line 86. The pump 71 is driven by suitable motor means 72 for pumping fluid through the pipe section 92 at a Reynolds number substantially the same as the Reynolds number determined for the flow rate being injected down the wellbore conduit 54. A second flow meter 74 is also interposed between the second pump 71 and the turbulent flow pipe viscometer 92 for measuring flow rate and determining required velocity to obtain the flow regime comparable to the flow regime in the conduit 54. The turbulent flow pipe viscometer 92 also includes an arrangement of pressure transducers 88 for measuring pressure drop across a predetermined length of the pipe section 92. The pipe section 92 is connected by suitable removable bolt type flanges 93 and 95 into the flow path formed between the conduit section 94 and the second pump 71 and may be replaced by other pipe sections, such as a section 97, having a suitable arrangement of pressure differential measuring transducers 88 mounted thereon and wherein said other pipe sections have different effective diameter or hydraulic radius and surface roughness characteristics.

As indicated in FIG. 1, the pressure transducers 88, the flow meter 66, the fluid density meter 76 and the flow meters 74 may be adapted to generate suitable electrical signals which are transmitted to a signal conversion unit 98 wherein suitable digital signals are produced for inputting to a digital computer 100 whereby a substantially continuous reading of pressure and flow conditions in the vicinity of the perforations 52 may be produced. In this regard, a suitable static pressure transducer 89 is also preferably located at the inlet to the conduit 54 at the wellhead 17 and wherein the output signal from this pressure transducer is also transmitted to the signal converter unit 98.

The basic method of determining friction pressure losses through the conduit 54 may be carried out using the apparatus 14 on a continuous basis, assuming that calculations can be made rapidly, such as by the computer 100, while fracturing fluids are being pumped through the conduit 54 from the supply source such as the blending tank 18 by way the apparatus 14. While fracturing fluids are being pumped at the prescribed flow rate by the pumps 38 from the tank 18 through the manifold 60, the flow conduit 64 and the manifold 62, the fluid flowing through the conduit 64 may be continuously or intermittently sampled by the laminar flow viscometer and turbulent flow viscometer means connected to the conduit 64 while a major portion of the fluid is pumped directly through the conduit 64 from the manifold 60 to the manifold 62.

For example, the diameters and lengths of the conduit sections 68, 80 and 82 are known over which pressure drops are being measured by the respective sets of transducers 88, the flow rate through the continuous pipe loop which includes these conduit sections may be determined by the flow meter 74 and the density of the fluid being pumped may also be measured by the density meter 76. Values of velocity in each of the pipe sections 68, 80 and 82 may be measured, since their diameters are known and the flow rate may be determined from the flow meter 74, using the equation:

$$Q = 0.785 \, D^2 V \tag{6}$$

wherein flow rate Q is expressed in ft.$^3$/min., D = ft. and V = ft./min.

Since the diameters of the pipe sections 68, 80 and 82 are known, over which the pressure drops are being measured, and the respective lengths are known, the equation for shear stress and the equation for shear rate may be solved for the flow conditions in each of the pipe sections 68, 80 and 82. These values of shear stress $\tau$, and shear rate $\gamma$, may be suitably plotted to determine the consistency index (K') and the flow behavior index (n'). These values of the respective indices are then used to determine the Reynolds number of the flow through the conduit 54 since the diameter of this conduit is known and the velocity may be determined from the measurements taken of the flow meter 66. Those skilled in the art will recognize that the flow meter 66 may be disposed in the conduit 54 or somewhere in the conduit 42 although its location on the apparatus 14 gives an indication of total flow being pumped through the conduit 54 minus any leakage losses in the pumps 38 or the conduits interconnecting these pumps with the apparatus 14 and the wellhead 17.

When the Reynolds number ($N'_{Re}$) is determined using equation (3) above, the flow rate through the pipe section 92 is determined by solving equation (3) for the velocity (V) required to produce the same Reynolds number. The values of pipe diameter (D), fluid density $\rho$, and the rheological parameters or indices (K') and (n') have been determined. The pump 71 may be operated at variable speeds or otherwise operated to provide a suitable displacement rate which will provide the required flow velocity in the pipe section 92.

When the prescribed flow velocity (V) is obtained in the turbulent pipe viscometer, comprising the pipe section 92, the friction pressure differential is measured by the arrangement of transducers 88 disposed on the pipe section 92 and the value of the Fanning friction factor (f) is determined using equation (4) hereinabove. This equation is then used to determine the pressure drop from the transducer 89 located at the wellhead 17 to the lower end of the conduit 54, since the (D) diameter and the length (L) of the conduit 54 are known, the density (p) of the fluid being pumped is known and the velocity (V) may be known from the flow rate measured by the flow meter 66.

Accordingly, continuous and relatively accurate calculations of friction pressure loss may be obtained in accordance with the aforedescribed method using the apparatus 14 in a system as described herein in conjunction with FIG. 1.

Those skilled in the art will also recognize that the apparatus 14 could be modified to provide a viscometer apparatus which basically utilizes only the second pump 71 and the pipe viscometer having the pipe section 92 therein. For example, the pump 71 could be operated at variable speed or by other suitable means to provide variable displacement of fluid through the pipe viscometer 92 to provide the respective values required to solve equations (1) and (2) for shear stress and shear rate values needed to determine consistency index (K') and flow behavior or Power Law Index (n') values. Then the pump 71 could be operated to provide flow through the pipe viscometer 92 at the Reynolds number or in accordance with another suitable parameter which would provide the same flow regime in the pipe viscometer 92 as exists in the conduit 54 during fracturing operations.

Assuming that the pipe viscometer 92 only is used to determine the Fanning friction fractor (f) a procedure would be carried out generally as follows. The pump 71 would be operated at a flow displacement through the pipe viscometer section 92 which, from predetermined values of the consistency index (K') and the flow behavior index (n') would assure laminar flow for three separate pressure drop measurements at three separate flow rates through the pipe viscometer section 92. The pump 71 would be operated at a first flow rate in the laminar flow range for which a pressure drop between the spaced apart pressure transducers 88 on pipe section 92 would be measured. The values of diameter (D), pipe section length (L) between the arrangement of differential transducers 88 on pipe section 92 and velocity (V) of fluid flow through the pipe section 92 would be known or measurable quantities which would then be used to solve the equations (1) and (2) for values of shear stress and shear rate.

This process could be repeated at least two or three times at different flow velocities within the laminar flow regime to provide respective values of $\Delta P$.

After a suitable number of laminar flow measurements have been made to plot line 10 in FIG. 2 so as to determine the consistency index (K') and the flow behavior index (n') and the Reynolds number of the fluid being pumped through the conduit 54 has been calculated using equation (3), for example, the flow rate through the pipe viscometer section 92 would be increased to a flow velocity which would provide the same Reynolds number in the pipe section 92 as exists in the conduit section 54. The friction fluid pressure loss ($\Delta P$) between the transducers 88 in the pipe section 92 would then be measured at the Reynolds number condition of flow equivalent to that in the conduit section 54 to solve equation (4) for the Fanning friction factor (f). Equation (5) would then be used to determine the expected friction pressure loss between the transducer 89 at the wellhead 17 and the general area of the perforations 52 in the wellbore. The repeated sampling process using only a single pipe viscometer section 92 could be carried out at relatively high rates using electronic digital computing equipment to provide essentially continuous monitoring of the changes in the condition of the fluid being pumped through the apparatus 14 and to the wellhead 17.

Although preferred methods and apparatus according to the present invention have been described herein in detail, those skilled in the art will recognize that various substitutions and modifications could be made to the methods and the apparatus without departing from the scope and spirit of the present invention as recited in the appended claims.

What is claimed is:

1. In an operation for stimulating a subterranean formation to produce recoverable minerals, a method for determining friction pressure losses in a well flow conduit through which a non-Newtonian or generalized Newtonian stimulation fluid is being pumped, at a predetermined rate comprising the steps of:

providing high pressure pump means in communication with a source of said fluid;

providing viscometer apparatus interposed between said high pressure pump means and said source, said viscometer apparatus including conduit means of known length and diameter and a pipe viscometer section having a surface roughness similar to the surface roughness of said flow conduit;

pumping at least a sample of said fluid through said conduit means on said viscometer apparatus at plural known velocities and measuring the pressure differential due to friction over said known length;

calculating the generalized shear stress and shear rate for said plural velocities and pressure differentials due to friction losses;

determining the consistency index (K') and the Power Law Index (n') for said fluid from the respective sets of values of shear stress and shear rate;

determining the Reynolds number of the fluid flowing through said flow conduit and conducting at least a sample of said fluid through said viscometer section under the same conditions of Reynolds number;

measuring the friction pressure loss, the fluid density, and the velocity of fluid flow through said viscometer section;

calculating the value of the Fanning Friction factor (f) based on the measured values of friction pressure loss, fluid density, fluid velocity and the effective diameter and length of said viscometer section; and determining the friction pressure loss through said flow conduit by measuring the effective diameter of said flow conduit, the effective length of said flow conduit, the velocity of fluid flow through said flow conduit and using said friction factor and said measured value of fluid density.

2. The method set forth in claim 1 wherein:
the step of pumping said fluid through said conduit means comprises providing said conduit means as a continuous length of conduit having discrete portions of different diameter and measuring the pressure differential due to friction over separate predetermined lengths of said discrete portions, respectively, at a predetermined flow rate through said conduit means.

3. The method set forth in claim 2 wherein:
said predetermined flow rate is conducted at a Reynolds number of said fluid which provides for substantially laminar flow of fluid through said discrete portions of said conduit means.

4. The method set forth in claim 1 wherein:
said conduit means of known length and diameter and said viscometer section comprise a common length of pipe having means for measuring a pressure differential due to friction across said known length, and the step of pumping said at least a sample of fluid comprises pumping said fluid through said viscometer section at selected flow rates to provide said plural conditions of fluid flow velocity and pressure differential due to friction losses.

5. Apparatus for determining pressure losses in a conduit such as a well injection pipe through which non-Newtonian fluids are being pumped from a source to said well injection pipe by high pressure pump means, said apparatus comprising:
a main flow conduit interconnecting said source with said high pressure pump means;
a friction pressure differential measuring flow loop comprising a continuous length of conduit for conducting a sample of fluid flowing through said main flow conduit through said flow loop at a predetermined flow rate;
means for measuring a pressure differential across a predetermined length of conduit of said flow loop;
means for measuring the flow rate of fluid through said flow loop; and
a turbulent flow viscometer including a section of viscometer pipe having at least about the same surface roughness as said well injection pipe and means for measuring a pressure differential of fluid flow through a predetermined length of said section of viscometer pipe, said section of viscometer pipe being connected for conducting at least a sample of fluid flow from said main flow conduit at a selected rate of flow.

6. The apparatus set forth in claim 5 wherein:
said flow loop includes a pump for pumping fluid through said predetermined length of conduit of said flow loop at various preselected rates of flow for taking selected pressure differential readings with said pressure differential measuring means.

7. The apparatus set forth in claim 5 wherein:
said flow loop comprises plural discrete portions of conduit connected in series, each of said discrete portions having a diameter different from the diameter of the other discrete portions, and each of said discrete portions having a predetermined length of conduit, and means for measuring a pressure differential of fluid flowing through said predetermined length of conduit, respectively.

8. The apparatus set forth in claim 4 including:
pump means for pumping fluid through said section of viscometer pipe at a selected rate of flow.

9. The apparatus set forth in claim 5 including:
means for measuring the density of fluid flowing through said main flow conduit to said well injection pipe.

10. The apparatus set forth in claim 5 including:
means for measuring the flow rate of fluid flowing to said well injection pipe from said source.

11. Apparatus for measuring certain fluid properties of a liquid composition for injection into a subterranean formation through an elongated well injection pipe extending within a wellbore, said apparatus comprising:
first and second spaced apart manifold members, one of said manifold members being adapted to be connected to a source of liquid composition for injection into said well injection pipe and the other of said manifold members being adapted to be connected to means for pumping said liquid composition to said well injection pipe;
a main flow conduit interconnecting said first and second manifold members, said main flow conduit including fluid flow meter means interposed therein;
a branch conduit connected to said main flow conduit for receiving fluid from said main flow conduit, said branch conduit being connected to viscometer means for measuring the viscosity of a sample of liquid composition withdrawn from said main flow conduit, said branch conduit further including a densimeter for measuring the density of said liquid composition, and pump means connected to said branch conduit for pumping a sample of said liquid composition through said densimeter and said viscometer so that a sample of the liquid composition being conducted from said source to said well injection pipe may be continuously sampled for measurement of density and properties of said liquid composition related to the viscosity of said liquid composition, said apparatus being adapted to be interposed between said source of said liquid composition and said pump means for continuously measuring the flow rate of said liquid composition, the density of said liquid composition in properties related to the viscosity of said liquid composition while said liquid composition is being injected into said well injection pipe.

12. The apparatus set forth in claim 11 wherein:
said means for measuring properties related to the viscosity of said liquid composition includes a continuous length of conduit connected to said branch conduit, said continuous length including sections of conduit of different diameter and different cross sectional flow area, pressure differential measuring means for measuring pressure differential due to friction flow losses along certain portions of the length of said section of conduit at a substantially constant flow rate of liquid through said conduit section.

13. In an operation for stimulating a subterranean formation to produce at least one of oil or gas, a method for determining friction pressure losses in a well flow conduit through which a non-Newtonian or generalized Newtonian stimulation fluid is being pumped at a predetermined rate comprising the steps of:

providing high pressure pump means in communication with a source of said fluid;

providing viscometer apparatus interposed between said high pressure pump means and said source, said viscometer apparatus including a viscometer comprising conduit means of known length and effective diameter;

pumping at least a sample of said fluid through said conduit means at plural known velocities and measuring the pressure differential due to friction over said known length;

calculating the generalized shear stress and shear rate for said plural velocities and pressure differentials due to friction losses;

determining the consistency index ($K'$) and the Power Law Index ($n'$) for said fluid from the respective sets of values of shear stress and shear rate;

calculating the Reynolds number of the fluid flowing through said flow conduit using said consistency index and said Power Law index;

conducting at least a sample of said fluid through said viscometer under the same conditions of Reynolds number;

measuring the friction pressure loss, the fluid density, and the velocity of fluid flow through said viscometer;

calculating the value of the Fanning Friction factor (f) based on the measured values of friction pressure loss, fluid density, fluid velocity and the effective diameter and length of said viscometer; and calculating the friction pressure loss through said flow conduit by measuring the effective diameter of said flow conduit, the effective length of said flow conduit, the velocity of fluid flow through said flow conduit and using said friction factor and said measured value of fluid density.

* * * * *